United States Patent
Kanios et al.

(10) Patent No.: US 8,865,207 B2
(45) Date of Patent: *Oct. 21, 2014

(54) COMPOSITIONS AND METHODS FOR DELIVERING ACTIVE AGENTS IN TRANSDERMAL DRUG DELIVERY SYSTEMS

(71) Applicant: Noven Pharmaceuticals, Inc., Miami, FL (US)

(72) Inventors: David Kanios, Palmetto Bay, FL (US); Rod Hartwig, Cooper City, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/715,276

(22) Filed: Dec. 14, 2012

(65) Prior Publication Data

US 2013/0317461 A1   Nov. 28, 2013

Related U.S. Application Data

(63) Continuation of application No. 11/245,084, filed on Oct. 7, 2005, now Pat. No. 8,343,538.

(60) Provisional application No. 60/616,862, filed on Oct. 8, 2004.

(51) Int. Cl.
| | |
|---|---|
| *A61F 13/02* | (2006.01) |
| *A61L 15/16* | (2006.01) |
| *A61K 9/70* | (2006.01) |
| *A61F 13/00* | (2006.01) |

(52) U.S. Cl.
CPC ............ *A61K 9/7084* (2013.01); *A61K 9/7061* (2013.01)
USPC ............................. 424/448; 424/449; 424/443

(58) Field of Classification Search
None
See application file for complete search history.

(56) References Cited

U.S. PATENT DOCUMENTS

| | | |
|---|---|---|
| 4,390,520 A | 6/1983 | Nagai et al. |
| 4,559,222 A | 12/1985 | Enscore et al. |
| 4,584,355 A | 4/1986 | Blizzard et al. |
| 4,585,836 A | 4/1986 | Homan et al. |
| 4,591,622 A | 5/1986 | Blizzard et al. |
| 4,655,767 A | 4/1987 | Woodard et al. |
| 4,746,515 A | 5/1988 | Cheng et al. |
| 4,911,707 A | 3/1990 | Heiber et al. |
| 4,938,759 A | 7/1990 | Enscore et al. |
| 4,983,395 A | 1/1991 | Chang et al. |
| 4,994,267 A | 2/1991 | Sablotsky |
| 5,151,271 A | 9/1992 | Otsuka et al. |
| 5,271,940 A | 12/1993 | Cleary et al. |

(Continued)

FOREIGN PATENT DOCUMENTS

| | | |
|---|---|---|
| AU | 739141 | 1/1998 |
| EP | 1 449 527 A2 | 8/2004 |

(Continued)

OTHER PUBLICATIONS

Office Action issued Oct. 26, 2009, in U.S. Appl. No. 10/939,163 (US 2005/0129749).

(Continued)

*Primary Examiner* — Isis Ghali
(74) *Attorney, Agent, or Firm* — Foley & Lardner LLP (57) ABSTRACT

A blend of at least two polymers in combination with a drug provides a pressure-sensitive adhesive composition for a transdermal drug delivery system in which the drug is delivered from the pressure-sensitive adhesive composition and through dermis when the pressure-sensitive adhesive composition is in contact with human skin.

20 Claims, 2 Drawing Sheets

(56) References Cited

U.S. PATENT DOCUMENTS

| | | | |
|---|---|---|---|
| 5,350,581 | A | 9/1994 | Kochinke |
| 5,446,070 | A | 8/1995 | Mantelle |
| 5,474,783 | A | 12/1995 | Miranda et al. |
| 5,474,787 | A | 12/1995 | Grey et al. |
| 5,505,956 | A | 4/1996 | Kim et al. |
| 5,567,488 | A | 10/1996 | Allen et al. |
| 5,656,286 | A | 8/1997 | Miranda et al. |
| 5,665,377 | A | 9/1997 | Gonella |
| 5,730,999 | A | 3/1998 | Lehmann et al. |
| 5,762,952 | A | 6/1998 | Barnhart et al. |
| 5,837,280 | A | 11/1998 | Kenealy et al. |
| 5,902,603 | A | 5/1999 | Chen et al. |
| 5,904,931 | A | 5/1999 | Lipp et al. |
| 5,906,830 | A | 5/1999 | Farinas et al. |
| 5,928,666 | A | 7/1999 | Farinas et al. |
| 5,958,446 | A | 9/1999 | Miranda et al. |
| 5,997,897 | A * | 12/1999 | Horstmann et al. .......... 424/447 |
| 6,024,976 | A | 2/2000 | Miranda et al. |
| 6,221,383 | B1 | 4/2001 | Miranda et al. |
| 6,235,306 | B1 | 5/2001 | Miranda et al. |
| 6,562,363 | B1 | 5/2003 | Mantelle et al. |
| 6,808,739 | B2 | 10/2004 | Sitz et al. |
| 8,187,628 | B2 | 5/2012 | Houze et al. |
| 8,216,606 | B2 | 7/2012 | Houze et al. |
| 8,343,538 | B2 | 1/2013 | Kanios |
| 2001/0033858 | A1 | 10/2001 | Zhang |
| 2002/0100185 | A1 | 8/2002 | Sitz et al. |
| 2003/0228354 | A1 | 12/2003 | Muraoka et al. |
| 2005/0129749 | A1 | 6/2005 | Strauss |
| 2005/0169977 | A1 | 8/2005 | Kanios |
| 2006/0078603 | A1 | 4/2006 | Nguyen |
| 2011/0091511 | A1 | 4/2011 | Nguyen |

FOREIGN PATENT DOCUMENTS

| | | |
|---|---|---|
| WO | WO 91/03998 | 4/1991 |
| WO | WO 93/00058 A1 | 1/1993 |
| WO | WO 00/33812 | 6/2000 |
| WO | WO 01/26705 A2 | 4/2001 |

OTHER PUBLICATIONS

Office Action issued May 13, 2009, in U.S. Appl. No. 10/939,163 (US 2005/0129749).
Office Action issued Oct. 16, 2008, in U.S. Appl. No. 10/939,163 (US 2005/0129749).
Office Action issued May 22, 2008, in U.S. Appl. No. 10/939,163 (US 2005/0129749).
Office Action issued on Aug. 17, 2010 in U.S. Appl. No. 10/939,163 (US 2005/0129749).
Office Action issued on Mar. 1, 2010 in U.S. Appl. No. 10/939,163 (US 2005/0129749).
Office Action issued on Sep. 16, 2013 in U.S. Appl. No. 10/939,163 (US 2005/129749).
Notice of Allowance issued on Mar. 13, 2014 in U.S. Appl. No. 10/939,163 (US 2005/0129749).
Office Action issued Jun. 11, 2008, in U.S. Appl. No. 10/975,043 (US 2005/0169977).
Office Action issued Jun. 26, 2009, U.S. Appl. No. 10/975,043 (US 2005/0169977).
Office Action issued on Feb. 3, 2010 in U.S. Appl. No. 10/975,043 (US 2005/0169977).
Office Action issued on Oct. 13, 2010 in U.S. Appl. No. 10/975,043 (US 2005/0169977).
Office Action issued on Jan. 25, 2011 in U.S. Appl. No. 10/975,043 (US 2005/0169977).
Office Action issued on Oct. 2, 2013 in U.S. Appl. No. 10/975,043 (US 2005/0169977).
Notice of Allowance issued on Dec. 4, 2013 in U.S. Appl. No. 10/975,043 (US 2005/0169977).
International Search Report issued Apr. 6, 2005 for application No. PCT/US2004/029789.
*Merck Index*, $12^{th}$ ed., Merck and Co., Rahway, New Jersey, pp. ther-1-ther-28 (1999).
*Merck Index*, $11^{th}$ ed., Merck and Co., Rahway, New Jersey, pp. ther-5-ther-29 (1980).
"Acrylic and Methacrylic Ester Polymers," *Polymer Science and Engineering*, vol. 1, $2^{nd}$ ed., pp. 234-269, John Wiley & Sons (1984).
Kurnik et al., "Modeling of diffusion and crystal dissolution in controlled release systems," Journal of Controlled Release, vol. 45, pp. 257-264, 1997.
Nitto Denko, "Advancing Drug Delivery Technologies," Business Week, Special Advertising Section, Mar. 29, 2004.
Office Action issued on Dec. 7, 2011 in U.S. Appl. No. 12/979,978 (US 2011/0091511).
Satas, "Acrylic Adhesives," Handbook of Pressure-Senstive Adhesive Technology, $2^{nd}$ ed., pp. 396-456, 1989.
Sobieski et al., "Silicone Pressure-Sensitive Adhesives," Handbook of Pressure-Senstive Adhesive Technology, $2^{nd}$ ed., pp. 508-517 (D.Satas, ed.), 1989.
Vaughan, "Using Solubility Parameters in Cosmetics Formulation," *J. Soc. Cosmet. Chem.*, vol. 36, pp. 319-333 (1985).
Notice of Allowance issued on May 30, 2012 in U.S. Appl. No. 11/256,190 (US 8,216,606).
Notice of Allowance issued on Apr. 11, 2012 in U.S. Appl. No. 11/256,190 (US 8,216,606).
Notice of Allowance issued on Dec. 16, 2011 in U.S. Appl. No. 11/256,190 (US 8,216,606).
Office Action issued on Oct. 11, 2011 in U.S. Appl. No. 11/256,190 (US 8,216,606).
Office Action issued on May 24, 201 in U.S. Appl. No. 11/256,190 (US 8,216,606).
Office Action issued on Nov. 8, 2010 in U.S. Appl. No. 11/256,190 (US 8,216,606).
Office Action issued on Jun. 18, 2009 in U.S. Appl. No. 11/256,190 (US 8,216,606).
Office Action issued on Feb. 4, 2009 in U.S. Appl. No. 11/256,190 (US 8,216,606).
Office Action issued on Aug. 20, 2008 in U.S. Appl. No. 11/256,190 (US 8,216,606).
Office Action issued on Mar. 28, 2008 in U.S. Appl. No. 11/256,190 (US 8,216,606).
Office Action issued on Nov. 30, 2007 in U.S. Appl. No. 11/256,190 (US 8,216,606).
Office Action issued on Mar. 5, 2007 in U.S. Appl. No. 11/256,190 (US 8,216,606).
Notice of Allowance issued on Apr. 12, 2012 in U.S. Appl. No. 11/256,189 (US 8,187,628).
Office Action issued on Nov. 9, 2010 in U.S. Appl. No. 11/256,189 (US,187,628).
Office Action issued on Sep. 8, 2009 in U.S. Appl. No. 11/259,189 (US 8,187,628).
Office Action issued on Mar. 13, 2009 in U.S. Appl. No. 11/256,189 (US 8,187,628).
Office Action issued on Mar. 5, 2008 in U.S. Appl. No. 11/256,189 (US 8,187,628).
Office Action issued on Jun. 11, 2007 in U.S. Appl. No. 11/256,189 (US 8,187,628).

* cited by examiner

COMPOSITIONS AND METHODS FOR DELIVERING ACTIVE AGENTS IN TRANSDERMAL DRUG DELIVERY SYSTEMS

This application claims the benefit of provisional application 60/616,862 filed Oct. 8, 2004, which is hereby incorporated by reference in its entirety.

FIELD OF THE INVENTION

This invention relates generally to transdermal drug delivery systems, and more particularly to pharmaceutically acceptable adhesive matrix compositions. The invention additionally relates to transdermal drug delivery systems providing substantially zero order drug release profiles for an extended period of time of up to seven days or longer.

BACKGROUND OF THE INVENTION

The present invention relates to transdermal delivery systems, their method of making and method of use. In particular, the present invention is directed to a transdermal drug delivery system for the topical application of one or more active agents contained in one or more polymeric and/or adhesive carrier layers, proximate to a non-drug containing polymeric and/or adhesive coating that is applied to either the transdermal system's backing or release liner. The adhesive coated backing or release liner may be processed or manufactured separately from the polymeric and/or adhesive drug carrier layers when drug loss or other system concerns are prevalent, and combined prior to topical application. The drug delivery rate and profile can be further controlled by adjusting certain characteristics of the polymers and/or adhesives themselves or of the method of making the system, relative to the active agent's properties in this transdermal system.

BACKGROUND OF THE INVENTION

The use of a transdermal drug delivery system as a means for administering therapeutically effective amounts of an active agent is well known in the art. Transdermal devices or systems can be categorized in many different ways, but those commonly called transdermal patches, incorporate the active agent into a carrier, usually a polymeric and/or a pressure-sensitive adhesive formulation.

Many factors influence the design and performance of such drug delivery devices, such as the individual drugs themselves, the physical/chemical characteristics of the system's components themselves and their performance/behavior relative to other system components once combined, external/environmental conditions during manufacturing and storage thereafter, the properties of the topical site of application, the desired rate of drug delivery and onset, the drug delivery profile, and the intended duration of delivery. Cost, appearance, size and ease of manufacturing are also important considerations. The ability to deliver a therapeutically effective amount of the drug in accordance with the intended therapy or treatment is the goal.

The simplest in design is one in which the drug is incorporated into a pressure-sensitive adhesive carrier layer, each surface of which is affixed to a polymeric film/layer—one serving as the backing (to anchor the carrier layer and control passage of environmental influences in and system components out during use) and the other serving as a removable liner (to protect the carrier layer prior to use but removed upon topical application of the carrier layer). However, when addressing all the design and performance factors and considerations to achieve the goal, this system alone cannot always provide the best method.

In this regard, a drug's delivery rate is affected by its degree of saturation and solubility in the carrier composition. Depending on the active agent itself or the dosage necessary to be therapeutically effective, the amount of drug needed to be incorporated into a single, adhesive carrier or matrix composition (i.e., drug loading) can adversely affect or be adversely affected by, such carrier or matrix.

Drug carrier compositions typically require one or more processing solvents, usually organic solvents, in which to incorporate the active agent and/or allow the polymeric/adhesive carrier to be more easily coated onto a backing or release liner. Removal of such solvents is necessary for avoiding problems associated with residual solvent amounts, such as irritation at the topical site of application, drug degradation, drug instability, loss of adhesive or cohesive properties impacting attachment of the system to the user and loss of desired delivery amount or rate. Solvent removal requires that elevated temperatures be applied to the carrier composition to evaporate such solvents. But at the same time, removal of solvents by use of elevated temperatures can also remove or evaporate other desirable components, such as the active agent and drug permeation enhancers. Their loss can even occur at temperatures below which such components may otherwise volatilize by virtue of their interaction with each other and with the other carrier components (relative volatility or reactivity).

Transdermal carrier compositions based on acrylic pressure-sensitive adhesive polymers are often preferred for their ability to incorporate or solubilize many drugs. In order to provide for adequate wear properties and drug release from the composition, acrylic-based pressure-sensitive adhesives are typically polymerized with functional monomers to provide functional groups on the acrylic-based adhesive. A problem associated with the use of such acrylic-based polymers with functional groups is that due to the generally high solubility of the drug, a large amount of drug generally must be incorporated into the composition to saturate it and provide an adequate drug release to the skin of the user. In use with low molecular weight drugs or controlled substances, the loss of the drug in the manufacturing process again can be a significant problem.

Attempts have been made to utilize rate controlling membranes and/or multiple layers, and to dissolve or suspend certain drugs in thermoplastic type carrier compositions without the use of solvents. These drug delivery devices generally do not allow a great amount of flexibility in effectively controlling the release rate of a variety of drugs, which in turn also severely limits their therapeutic application, and are expensive or burdensome to manufacture. Moreover, multiple adhesive layers are often required to affix the other layers or membranes to each other, and/or to the site of topical application.

Thus, it would therefore be desirable to provide a system for use with many types of drugs, in which the permeation rate and profile can be easily adjusted while providing an active agent-containing carrier composition formulated in a simple and cost effective manner.

SUMMARY OF THE INVENTION

Based upon the foregoing, it is an object of the present invention to overcome the limitations of the prior transdermal systems, and to provide a transdermal drug delivery system which allows selective modulation of drug permeation and delivery rates and profiles.

Another object is to provide a transdermal system, which is simple and inexpensive to manufacture, while preventing or minimizing drug loss and/or other volatile components in the composition. The present invention provides a transdermal drug delivery system for the topical application of one or more active agents contained in one or more polymeric and/or adhesive carrier layers, proximate to a non-drug containing polymeric and/or adhesive coating that is applied to either the transdermal system's backing or release liner, manufactured to optimize drug loading while providing desirable adhesion to skin or mucosa as well as providing modulation of the drug delivery and profile.

The invention is further directed to a transdermal delivery system comprising a backing composite comprising a non-drug containing polymeric and/or adhesive coating affixed or applied to a drug-impermeable layer. An active agent carrier layer comprising a pressure-sensitive adhesive composition and a drug incorporated therein, which may also contain low boiling point or volatile components such as permeation enhancers, is affixed to the backing composite. The polymeric coating is designed to provide control of permeation rate, onset and profile of the active agent from the system. The agent-carrier composition may comprise one or more layers. The agent-carrier composition may comprise at least one layer formed of a blend of at least one acrylic-based polymer and at least one silicone-based polymer, to serve as a pressure-sensitive adhesive composition for applying the system to the dermis, or a blend of acrylic-based polymers. The non-drug containing acrylic-based or other polymer coating designed to interact with the drug composition layer(s).

The invention is also directed to compositions and methods of controlling drug delivery rates, onset and profiles of at least one active agent in a transdermal delivery system, comprising the use of a non-drug containing acrylic-based polymer and/or adhesive coating one surface of which is applied to either the transdermal system's backing or release liner and the other surface is affixed to a drug containing carrier composition layer, wherein the delivery rate, onset of delivery (lag time) and delivery profile of a drug may be selectively modulated by one or more of (a) increasing or decreasing the thickness or coat weight of the acrylic-based polymer and/or adhesive coating per cm² as applied to the backing or release liner of the system or (b) manipulating the moiety or functionality of the acrylic-based polymer and/or adhesive coating. Either the non-drug containing coating or the carrier composition must also be a pressure-sensitive adhesive when used as area of attachment to the skin or mucosa of the user. The drug carrier composition may be comprised of (a) one or more acrylic-based polymers having one or more functionality or (b) one or more silicone-based polymers having one or more silanol contents (capping) and/or resin to polymer ratios, alone or in combination, and are present in proportions to provide a desired solubility for the drug. Further manipulation of drug delivery, onset and profiles can be achieved by varying the concentrations of the drug in the drug-loaded carrier.

For a better understanding of the present invention, together with other and further objects thereof, reference is made to the following description, taken in conjunction with the accompanying drawings, and its scope will be pointed out in the appending claims.

DETAILED DESCRIPTION OF THE PREFERRED EMBODIMENTS

In the following description, embodiments of the invention are set forth, and terms are used in describing such embodiments, wherein:

The term "topical" or "topically" is used herein in its conventional meaning as referring to direct contact with an anatomical site or surface area on a mammal including skin, teeth, nails and mucosa.

The term "mucosa" as used herein means any moist anatomical membrane or surface on a mammal such as oral, buccal, vaginal, rectal, nasal or ophthalmic surfaces. Similarly, "skin" is meant to include mucosa, which further includes oral, buccal, nasal, rectal and vaginal mucosa.

The term "transdermal" refers to delivery, administration or application of a drug by means of direct contact with tissue, such as skin or mucosa. Such delivery, administration or application is also known as percutaneous, dermal, transmucosal and buccal.

As used herein, the terms "blend" and "mixture" are used herein to mean that there is no, or substantially no, chemical reaction or crosslinking (other than simple H-bonding) between the different polymers in the polymer matrix. However, crosslinking between a single polymer component is fully contemplated to be within the scope of the present invention.

The term "adhesive" means a substance, inorganic or organic, natural or synthetic that is capable of surface attachment at the intended topical application site by itself or functions as an adhesive by admixture with tackifiers, plasticizers, cross-linking agents or other additives. In the most preferred embodiment, the carrier of the present invention is a "pressure-sensitive adhesive" which refers to a viscoelastic material which adheres instantaneously to most substrates with the application of very slight pressure and remains permanently tacky. A polymer or dermal composition is a pressure-sensitive adhesive within the meaning of the term as used herein if it has the adhesive properties of a pressure-sensitive adhesive per se or functions as a pressure-sensitive adhesive by admixture with tackifiers, plasticizers, cross-linking agents or other additives.

As used herein, a "polymer composition of two or more polymers" is defined as a physical blend of at least two polymers and can include 3 or more polymers. The two or more polymers may include the acrylic-based polymers described herein and can optionally include other polymers discussed more fully below.

The term "acrylic-based" polymer is defined as any polyacrylate, polyacrylic, acrylate and acrylic polymer. The acrylic-based polymers can be any of the homopolymers, copolymers, terpolymers, and the like of various acrylic acids or esters. The acrylic-based polymers useful in practicing the invention are polymers of one or more monomers of acrylic acids and other copolymerizable monomers. The acrylic-based polymers also include copolymers of alkyl acrylates and/or methacrylates and/or copolymerizable secondary monomers. Acrylic-based polymers with functional groups as described more fully below, are copolymerized with functional monomers.

As used herein, "functionality" is broadly defined as a measure of the type and quantity of functional groups that a particular acrylic-based polymer has.

As used herein, "functional monomers or groups," are monomer units in acrylic-based polymers which have reactive chemical groups which modify the acrylic-based polymers directly or provide sites for further reactions. Examples of functional groups include carboxyl, epoxy and hydroxy groups.

As used herein "non-functional acrylic-based polymer" is defined as an acrylic-based polymer that has no or substantially no functional reactive moieties present in the acrylic. These are generally acrylic esters which can be copolymerized with other monomers which do not have functional groups, such as vinyl acetate.

The term "carrier" as used herein refers to any non-aqueous material known in the art as suitable for transdermal drug delivery administration, and includes any polymeric material into which an active agent may be solubilized in combination or admixture with the other ingredients of the composition. The polymeric materials preferably comprise adhesives and, in particular, pressure-sensitive adhesives. The carrier material is typically used in an amount of about 40% to about 95%, and preferably from about 50% to about 80%, by weight based on the dry weight of the total carrier composition.

The term "carrier composition" may also refer to enhancers, solvents, co-solvents and other types of additives useful for facilitating transdermal drug delivery.

The carrier compositions of the present invention can also contain one or more non-aqueous solvents and/or co-solvents. Such solvents and/or co-solvents are those known in the art, and are non-toxic, pharmaceutically acceptable substances, preferably non-aqueous liquids, which do not substantially negatively affect the adhesive properties or the solubility of the active agents at the concentrations used. The solvent and/or co-solvent can be for the active agent or for the carrier materials, or both.

Suitable solvents include volatile processing liquids such as alcohols (e.g., methyl, ethyl, isopropyl alcohols and methylene chloride); ketones (e.g., acetone); aromatic hydrocarbons such as benzene derivatives (e.g., xylenes and toluenes); lower molecular weight alkanes and cycloalkanes (e.g., hexanes, heptanes and cyclohexanes); and alkanoic acid esters (e.g., ethyl acetate, n-propyl acetate, isobutyl acetate, n-butyl acetate isobutyl isobutyrate, hexyl acetate, 2-ethylhexyl acetate or butyl acetate); and combinations and mixtures thereof. Other suitable co-solvents include polyhydric alcohols, which include glycols, triols and polyols such as ethylene glycol, diethylene glycol, propylene glycol, dipropylene glycol, trimethylene glycol, butylene glycol, polyethylene glycol, hexylene glycol, polyoxethylene, glycerin, trimethylpropane, sorbitol, polyvinylpyrrolidone, and the like. Alternatively, co-solvents may include glycol ethers such as ethylene glycol monoethyl ether, glycol esters, glycol ether esters such as ethylene glycol monoethyl ether acetate and ethylene glycol diacetate; saturated and unsaturated fatty acids, mineral oil, silicone fluid, lecithin, retinol derivatives and the like, and ethers, esters and alcohols of fatty acids. As will be described in more detail hereafter, the solvents or co-solvents used in accordance with the invention are desirably a low volatile solvent that does not require excessive temperatures for evaporation thereof.

The term "solubilized" is intended to mean that in the carrier composition there is an intimate dispersion or dissolution of the active agent at the crystalline, molecular or ionic level, such that crystals of the active agent cannot be detected using a microscope having a magnification of 25.times.. As such, the active agent is considered herein to be in "non-crystallized" form when in the compositions of the present invention. In some embodiments, however, the carrier composition layer includes a therapeutically effective amount of one or more solid crystalline drugs incorporated therein.

As used herein "flux" is defined as the percutaneous absorption of drugs through the skin, and is described by Fick's first law of diffusion:

$$J = -D(dC_m/dx),$$

where J is the flux in $g/cm^2/sec$, D is the diffusion coefficient of the drug through the skin in $cm^2/sec$ and $dC_m/dx$ is the concentration gradient of the active agent across the skin or mucosa.

As used herein, "therapeutically effective" means an amount of an active agent that is sufficient to achieve the desired local or systemic effect or result, such as to prevent, cure, diagnose, mitigate or treat a disease or condition, when applied topically over the duration of intended use. The amounts necessary are known in the literature or may be determined by methods known in the art, but typically range from about 0.1 mg to about 20,000 mg, and preferably from about 0.1 mg to about 1,000 mg, and most preferably from about 0.1 to about 500 mg per human adult or mammal of about 75 kg body weight per 24 hours.

The term "about", and the use of ranges in general whether or not qualified by the term about, means that the number comprehended is not limited to the exact number set forth herein, and is intended to refer to ranges substantially within the quoted range not departing from the scope of the invention.

The term "user" or "subject" is intended to include all warm-blooded mammals, preferably humans.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

Figure 1:
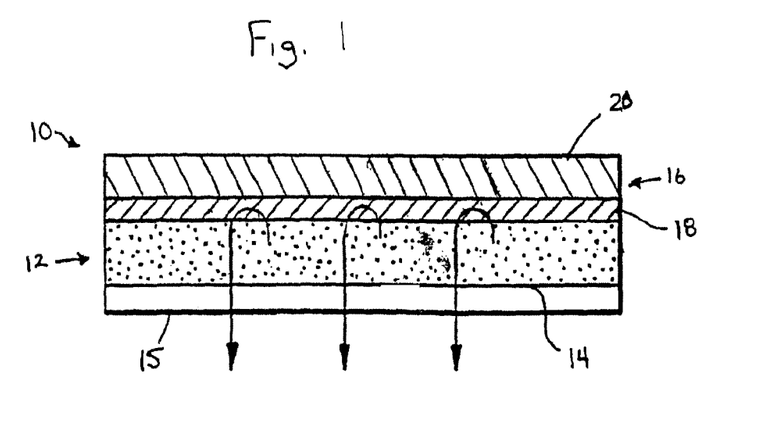
FIG. 1 shows a schematic cross-sectional view of a transdermal delivery device according to an embodiment of the invention prior to use.

Referring to FIG. 1, the most preferred embodiment of the invention, transdermal drug delivery system 10 comprises a carrier composition layer 12 incorporating the active agent. Surface 14 of the adhesive carrier composition layer 12 is affixed to release liner 15 to protect the carrier layer prior to use but which is removed upon topical application of the carrier layer to the skin or mucosa of the user. A non-drug containing polymeric and/or adhesive coating 18 is affixed to backing 20 on one surface, with the other surface being affixed to carrier composition layer 12. Backing composite 16 comprises coating 18 affixed to backing 20, which as described later, is made or processed separately from carrier composition layer 12 affixed to release liner 15.

Carrier composition layer 12 can comprise any polymer or adhesive generally known in the art for formulating a drug carrier composition, and include all of the non-toxic natural and synthetic polymers known or suitable for use in transdermal systems including solvent-based, hot melt and grafted adhesives, and may be used alone or in combinations, mixtures or blends. Examples include acrylic-based, silicone-based, rubbers, gums, polyisobutylenes, polyvinylethers, polyurethanes, styrene block copolymers, styrene/butadiene polymers, polyether block amide copolymers, ethylene/vinyl acetate copolymers, and vinyl acetate based adhesives, and bioadhesives set forth in U.S. Pat. No. 6,562,363 which is expressly incorporated by reference in its entirety.

The term "silicone-based" polymer is intended to be used interchangeably with the terms siloxane, polysiloxane, and silicones as used herein and as known in the art. The silicone-based polymer may also be a pressure-sensitive adhesive, with a polysiloxane adhesive prepared by cross-linking an elastomer, typically a high molecular weight polydiorganosiloxane, with a resin, to produce a three-dimensional siloxane structure, via a condensation reaction in an appropriate organic solvent. The ratio of resin to elastomer is a critical factor that can be adjusted in order to modify the physical properties of polysiloxane adhesives. Sobieski, et al., "Silicone Pressure Sensitive Adhesives," Handbook of Pressure-Sensitive Adhesive Technology. 2nd ed., pp. 508-517 (D. Satas, ed.), Van Nostrand Reinhold, New York (1989). Further details and examples of silicone pressure-sensitive adhesives which are useful in the practice of this invention are described in the following U.S. Pat. Nos. 4,591,622; 4,584,355; 4,585,836; and 4,655,767, all expressly incorporated by reference in their entireties. Suitable silicone pressure-sensitive adhesives are commercially available and include the silicone adhesives sold under the trademarks BIO-PSA® by Dow Corning Corporation, Medical Products, Midland, Mich. (such as -2685, -3027, -3122, -4101, -4102, -4203, -4301, -4302, -4303, -4401-4403, -4501, -4503, -4602, -4603 and -4919). Capped silicones with high resin content are preferred.

In the practice of the preferred embodiments of the invention, the acrylic-based polymer can be any of the homopolymers, copolymers, terpolymers, and the like of various acrylic acids. In such preferred embodiments, the acrylic-based polymer constitutes from about 2% to about 95% of the total dry weight of the of the carrier composition, and preferably from about 2% to about 90%, and more preferably from about 2% to about 85%, wherein the amount of the acrylic-based polymer is dependent on the amount and type of drug used.

The acrylic-based polymers usable in the invention are polymers of one or more monomers of acrylic acids and other copolymerizable monomers. The acrylate polymers also include copolymers of alkyl acrylates and/or methacrylates and/or copolymerizable secondary monomers or monomers with functional groups. By varying the amount of each type of monomer added, the cohesive properties of the resulting acrylate polymer can be changed as is known in the art. In general, the acrylate polymer is composed of at least 50% by weight of an acrylate or alkyl acrylate monomer, from 0 to 20% of a functional monomer copolymerizable with the acrylate, and from 0 to 40% of other monomers.

Acrylate monomers which can be used include acrylic acid, methacrylic acid, methyl acrylate, methyl methacrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate.

Functional monomers, copolymerizable with the above alkyl acrylates or methacrylates, which can be used include acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate and methoxyethyl methacrylate.

Suitable acrylic-based polymers may also be a pressure-sensitive adhesive which are commercially available and include the acrylic-based adhesives sold under the trademarks Duro-Tak® by National Starch and Chemical Corporation, Bridgewater, N.J. (such as 87-2287, -4098, -2852, -2196, -2296, -2194, -2516, -2070, -2353, -2154, -2510, -9085, -9088 and 73-9301). Other suitable acrylic-based adhesives include those sold by Cytec Surface Specialties, St. Louis, Mo., under the trademarks Gelva® Multipolymer Solution (such as 2480, 788, 737, 263, 1430, 1753, 1151, 2450, 2495, 3087 and 3235) and those under the trademark Eudragit® by Roehm Pharma GmbH, Darmstadt, Federal Republic of Germany.

The carrier composition may comprise blends of acrylic-based polymers, silicone-based polymers and rubbers based upon their differing solubility parameters, alone or in combination with other polymers, for example polyvinylpyrrolidone, as more fully described in U.S. Pat. Nos. 5,474,783; 5,656,286; 5,958,446; 6,024,976; 6,221,383; and 6,235,306; which are incorporated herein in their entirety. The amount of each polymer is selected to adjust the saturation concentration of the drug in the multiple polymer system, and to result in the desired rate of delivery of the drug from the system and through the skin or mucosa.

Combinations of acrylic-based polymers based on their functional groups is also contemplated. Acrylic-based polymers having functional groups are copolymers or terpolymers which contain in addition to nonfunctional monomer units, further monomer units having free functional groups. The monomers can be monofunctional or polyfunctional. These functional groups include carboxyl groups, hydroxy groups, amino groups, amido groups, epoxy groups, etc. Preferred functional groups are carboxyl groups and hydroxy groups. Preferred carboxyl functional monomers include acrylic acid, methacrylic acid, itaconic acid, maleic acid, and crotonic acid. Preferred hydroxy functional monomers include 2-hydroxyethyl methacrylate, 2-hydroxyethyl acrylate, hydroxymethyl acrylate, hydroxymethyl methacrylate, hydroxyethyl acrylate, hydroxyethyl methacrylate, hydroxypropyl acrylate, hydroxypropyl methacrylate, hydroxybutyl acrylate, hydroxybutyl methacrylate, hydroxyamyl acrylate, hydroxyamyl methacrylate, hydroxyhexyl acrylate, hydroxyhexyl methacrylate. Non-functional acrylic-based polymers can include any acrylic based polymer having no or substantially no free functional groups. The acrylic based polymer can include homopolymers, copolymers and terpolymers. The monomers used to produce the polymers can include alkyl acrylic or methacrylic esters such as methyl acrylate, ethyl acrylate, propyl acrylate, amyl acrylate, butyl acrylate, 2-ethylbutyl acrylate, hexyl acrylate, heptyl acrylate, octyl acrylate, nonyl acrylate, 2-ethylhexyl acrylate, decyl acrylate, dodecyl acrylate, tridecyl acrylate, glycidyl acrylate and the corresponding methacrylic esters.

Both the acrylic-based polymer having substantially no functional groups and acrylic-based polymers having functional groups can optionally include further modifying monomers. These modifying monomers can include any conceivable monomer that is capable of undergoing vinyl polymerization. For example, the incorporation of styrene monomers can be used to increase the glass transition temperature and are sometimes used to improve the cohesive strength. The copolymerization of vinyl acetate monomers with acrylic esters are also used to form acrylic-based polymers. Ethylene can also be copolymerized with acrylic esters and vinyl acetate to give suitable acrylic-based polymers.

For example, a composition will require less of a functional acrylic that contains 20% by weight of functional groups as opposed to one that contains 0.5% by weight of functional groups to achieve the same effect required for solubility and flux. Broadly speaking, the amount of functional acrylic is generally within the range of about 1 to 99 weight % and preferably 5 to 95 weight %, more preferably 20 to 75 weight %, even more preferably 30 to 65 weight %, based on the total polymer content of the transdermal composition. The amount of non-functional acrylic or acrylic with a functional group which does not have as great of an affinity for the drug, is within the range of about 99 to 1 weight %, preferably 95 to 5 weight %, more preferably 75 to 20 weight % and even more preferably 30 to 65 weight %, based on the total polymer content of the composition.

Further details and examples of acrylic-based adhesives, functional monomers, and polymers which have no functional groups and which are suitable in the practice of the invention are described in Satas, "Acrylic Adhesives," Handbook of Pressure-Sensitive Adhesive Technology, 2nd ed., pp. 396-456 (D. Satas, ed.), Van Nostrand Reinhold, N.Y. (1989); "Acrylic and Methacrylic Ester Polymers," Polymer Science and Engineering, Vol. 1, 2nd ed., pp 234-268, John Wiley & Sons, (1984); U.S. Pat. No. 4,390,520; and U.S. Pat. No. 4,994,267 all of which are expressly incorporated by reference in their entireties.

The required proportions of acrylic-based or other polymers used are generally dependant on the specific drug, its desired delivery rate and the desired duration of drug delivery. In general, proportions of acrylic-based polymers also depend on the content of the functional monomer units in the functional acrylic.

When the drug carrier composition is intended to function as the face layer, that is the layer that comes in contact with the topical site of application as depicted in FIG. 1, it is preferable that the carrier composition comprise a pressure-sensitive adhesive or bioadhesive.

In transdermal systems according to the invention, the drug carrier composition is designed to provide selectable modulation of delivery rates, onset and profiles of the drug when used in combination with a non-drug containing polymeric and/or adhesive coating that is applied to either the transdermal system's backing or release liner. Minimizing or preventing drug loss is also desirable when trying to deliver controlled substances and/or drugs that are easily volatilized and/or degraded during the manufacture of the transdermal delivery system, for example where there is high or excess drug concentration or loading in the carrier composition or where the drug degrades from exposure to atmospheric air or oxygen.

Any molecular weight drug and its equivalent forms can be used in the present invention. The preferred drug is one that is hydrophilic and not relatively volatile or reactive with the other carrier components, but which is incorporated into a carrier composition with certain co-solvents or enhancers preferred for use with such drugs that would be, by their own properties or by virtue of their relative volatility or reactivity with the other carrier components, substantially unstable or substantially evaporated or driven-off at the temperatures generally known or used in the art to remove solvents during the manufacturing processing, typically in the range of 160° F. to 250° F.

The drugs and mixtures thereof can be present in the composition in different forms, depending on which yields the optimum delivery characteristics. Thus, in the case of drugs, the drug can be in its free base or acid form, or in the form of salts, esters, amides, prodrugs, enantiomers or mixtures thereof, or any other pharmacologically acceptable derivatives, or as components of molecular complexes.

Any drug suitable for transdermal administration by methods previously known in the art and by the methods of the present invention can be used in the present invention, and further include such active agents that may be later established as drugs and are suitable for delivery by the present invention. These drugs include but are not limited to those categories and species of drugs set forth on page ther-1 to ther-28 of the Merck Index, 12th Edition Merck and Co. Rahway, N.J. (1999). This reference is incorporated by reference in its entirety. Exemplary of drugs that can be administered by the novel dermal drug delivery system include, but are not limited to:

1. Central nervous system stimulants and agents such as Dextroamphetamine, Amphetamine, Methamphetamine, D-Amphetamine, Phentermine, Methylphenidate and Nicotine.

2. Analgesics and/or Anti-Migraine such as Acetaminophen, Acetylsalicylic Acid, Buprenorphine, Codeine, Fentanyl, Lisuride, Salicylic Acid derivatives and Sumatriptan.

3. Androgen agents such as Fluoxymesterone, Methyl Testosterone, Oxymesterone, Oxymetholone, Testosterone and Testosterone derivatives.

4. Anesthetic agents such as Benzocaine, Bupivicaine, Cocaine, Dibucaine, Dyclonine, Etidocaine, Lidocaine, Mepivacaine, Prilocaine, Procaine and Tetracaine.

5. Anoretic agents such as Fenfluramine, Mazindol and Phentermine,

6. Anti-Bacterial (antibiotic) agents including Aminoglycosides, β-Lactams, Cephamycins, Macrolides, Penicillins, Polypeptides and Tetracyclines.

7. Anti-Cancer agents such as Aminolevulinic Acid and Tamoxifen.

8. Anti-Cholinergic agents such as Atropine, Eucatropine and Scopolamine.

9. Anti-Diabetic agents such as Glipizide, Glyburide, Glypinamide and Insulins.

10. Anti-Fungal agents such as Clortrimazole, Ketoconazole, Miconazole, Nystatin and Triacetin.

11. Anti-Inflammatory and/or Corticoid agents such as Beclomethasone, Betamethasone, Betamethasone Diprprionate, Betamethasone Valerate, Corticosterone, Cortisone, Deoxycortocosterone and Deoxycortocosterone, Acetate, Diclofenac, Fenoprofen, Flucinolone, Fludrocortisone, Fluocinonide, Fluradrenolide, Flurbiprofen, Halcinonide, Hydrocortisone, Ibuprofen, Ibuproxam, Indoprofen, Ketoprofen, Ketorolac, Naproxen, Oxametacine, Oxyphenbutazone, Piroxicam, Prednisolone, Prednisone, Suprofen and Triamcinolone Acetonide.

12. Anti-Malarial agents such as Pyrimethamine.

13. Anti-Parkinson's and/or Anti-Alzhiemer's agents such as Bromocriptine, 1-Hydroxy-Tacrine, Levodopa, Lisaride Pergolide, Pramipexole, Ropinirole, Physostigimine, Tacrine Hydrochloride and Teruride.

14. Anti-Psychotic and/or Anti-Anxiety agents such as Acetophenazine, Azapirones, Bromperidol, Chlorproethazine, Chlorpromazine, Fluoxetine, Fluphenazine, Haloperidol, Loxapine, Mesoridazine, Molindone, Ondansetron, Perphenazine, Piperacetazine, Thiopropazate, Thioridazine, Thiothixene, Trifluoperazine and Triflupromazine.

15. Anti-Ulcerative agents such as Enprostil and Misoprostol.

16. Anti-Viral agents such as Acyclovir, Rimantadine and Vidarabine.

17. Anxiolytic agents such as Buspirone, Benzodiazepines such as Alprazolam, Chlordiazepoxide, Clonazepam, Clorazepate, Diazepam, Flurazepam, Halazepam, Lorazepam, Oxazepam, Oxazolam, Prazepam and Triazolam.

18. β-Adrenergic agonist agents such as Albuterol, Carbuterol, Fenoterol, Metaproterenol, Rimiterol, Quinterenol, Salmefamol, Soterenol, Tratoquinol, Terbutaline and Terbuterol.

19. Bronchodilators such as Ephedrine derivatives including Epiniphrine and Isoproterenol, and Theophylline.

20. Cardioactive agents such as Atenolol, Benzydroflumethiazide, Bendroflumethiazide, Calcitonin, Captopril, Chlorothiazide, Clonidine, Dobutamine, Dopamine, Diltiazem, Enalapril, Enalaprilat, Gallopamil, Indomethacin, Isosorbide Dinitrate and Mononitate, Nicardipine, Nifedipine, Nitroglycerin, Papaverine, Prazosin, Procainamide, Propranolol, Prostaglandin $E_1$, Quinidine Sulfate, Timolol, and Verapamil.

21. α-Adrenergic agonist agents such as Phenylpropanolamine.

22. Cholinergic agents such as Acetylcholine, Arecoline, Bethanechol, Carbachol, Choline, Methacoline, Muscarine and Pilocarpine.

23. Estrogens such as Conjugated Estrogenic Hormones, Equilenin, Equilin, Esterified Estrogens, Estradiol, 17β-Estradiol, Estradiol Benzoate, 17β-Estradiol Valerate, Estradiol 17β-Cypionate, Estriol, Estrone, Estropipate, 17β-Ethinyl Estradiol and Mestranol.

24. Muscle relaxants such as Baclofen.

25. Narcotic antagonist agents such Nalmfene and Naloxone.

26. Progestational agents such as Chlormadinone and Chlormadinone Acetate, Demegestone, Desogestrel, Dimethisterone, Dydrogesterone, Ethinylestrenol, Ethisterone, Ethynodiol and Ethynodiol Diacetate, Gestodene, 17α-Hydroxyprogesterone, Hydroxygesterone Caproate, Medroxyprogesterone and Medroxyprogesterone Acetate, Megestrol Acetate, Melengestrol, Norethindrone and Norethidrone Acetate, Norethynodrel, Norgesterone, Norgestrel, 19-Norprogesterone, Progesterone, Promegestone and esters thereof. Free base forms of drugs which have a greater affinity for the acid (carboxyl) functional group in a carboxyl functional acrylic-based polymer are preferred in some applications.

For most drugs, their passage through the skin or mucosa will be the rate-limiting step in delivery. Thus, the amount of drug and the rate of release is typically selected so as to provide delivery characterized by a pseudo-zero order time dependency for a prolonged period of time. The minimum amount of drug in the system is selected based on the amount of drug which passes through the skin or mucosa in the time span for which the device is to provide a therapeutically effective amount. Generally, the amount of drug in the transdermal system can vary from about 0.1 to 40% by weight, preferably 0.5 to 30% by weight, and optimally 1-20% weight percent, based on the total dry weight of the agent-carrier composition.

The inventors have found that by separately preparing and processing the drug carrier composition and the non-drug loaded polymeric or adhesive coating (applied to either the backing or the release liner), greater flexibility can be achieved in controlling delivery rates and profiles. For example, typical carrier compositions prepared with acrylic-based polymers or blend of polymers for a transdermal delivery device require coat weights of about 10 mg/cm² to achieve the desired drug loading and adhesive characteristics. In the present invention, the coat weight of a carrier composition for delivering at least one drug at a similar flux may be reduced to about 5 mg/cm², or about one-half the coat weight of prior systems.

The polymeric coating 18 may comprise one or more of the polymers or adhesives described with reference to the drug carrier composition, generally with higher percent solids, but contain no active agent during its exposure to elevated temperatures for solvent removal prior to being affixed to the drug carrier composition. Preferred are non-functional, acrylic-based adhesives. The polymeric coating is disposed on either the backing or release liner and generally at a thickness so that the coat weight ranges from about 2.5 m g/cm² to about 15 mg/cm².

Once affixed to the carrier composition, the non-drug loaded polymeric or adhesive coating serves to absorb or attract and retain amounts of drug from the drug carrier composition, and subsequently release drug upon topical application of the transdermal system. This process further allows for potentially higher drug loading in the carrier composition, where desired or needed, for example to deliver drugs requiring higher amounts to be therapeutically effective and/or to deliver therapeutically effective amounts over a longer period of delivery, since any excess solubilized drug or supersaturated or highly concentrated drug will be absorbed or drawn away thereby permitting the carrier composition to maintain its desired adhesive properties while still providing desired permeation rate and profile to be achieved.

The polymeric coating can further be prepared to selectively control the desired delivery rate, onset and profile for the drug by varying certain other physical characteristics. As demonstrated in the examples employing an acrylic-based adhesive coating, the delivery rate, onset of delivery (lag time) and delivery profile of estradiol from the transdermal system may be selectively modulated by one or more of (a) increasing or decreasing the thickness or coat weight of per cm² (as applied to the backing or release liner of the system) or (b) manipulating the moiety or functionality.

While one or more acrylic-based adhesives are preferred for use as the non-drug loaded coating, other polymers, alone or in combination, may be used provided such polymers have the ability to (a) incorporate and hold drug from the drug-loaded carrier composition after manufacture, (b) maintain contact/adhesion to both the carrier composition and either the backing film/layer or the release liner, preferably without the use of additional adhesives, (c) not degrade or interfere with stability of the drug, and (d) release or deliver the drug to the skin or mucosa after topical application of the transdermal system.

In certain embodiments of the invention, an enhancer can be incorporated into either the carrier composition or the polymeric coating, or both. The term "enhancers" as used herein refers to substances used to increase permeability and/or accelerate the delivery of an active agent through the skin or mucosa, and include monhydric alcohols such as ethyl, isopropyl, butyl and benzyl alcohols; or dihydric alcohols such as ethylene glycol, diethylene glycol, or propylene glycol, dipropylene glycol and trimethylene glycol; or polyhydric alcohols such as glycerin, sorbitol and polyethylene glycol, which enhance drug solubility; polyethylene glycol ethers of aliphatic alcohols (such as cetyl, lauryl, oleyl and stearly) including polyoxyethylene (4) lauryl ether, polyoxyethylene (2) oleyl ether and polyoxyethylene (10) oleyl ether commercially available under the trademark BRIJ® 30, 93 and 97 from ICI Americas, Inc., and BRIJ® 35, 52, 56, 58, 72, 76, 78, 92, 96, 700 and 721; vegetable, animal and fish fats and oils such as cotton seed, corn, safflower, olive and castor oils, squalene, and lanolin; fatty acid esters such as propyl oleate, decyl oleate, isopropyl palmitate, glycol palmitate, glycol laurate, dodecyl myristate, isopropyl myristate and glycol stearate which enhance drug diffusibility; fatty acid alcohols such as oleyl alcohol and its derivatives; fatty acid amides such as oleamide and its derivatives; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered and esters of sorbitol and sorbitol anhydride such as polysorbate 20 commercially available under the trademark Tween® 20 from ICI Americas, Inc., as well as other polysorbates such as 21, 40, 60, 61, 65, 80, 81, and 85. Other suitable enhancers include oleic and linoleic acids, triacetin, ascorbic acid, panthenol, butylated hydroxytoluene, tocopherol, tocopherol acetate, tocopheryl linoleate. If enhancers are incorporated into the transdermal system, the amount typically ranges up to about 30%, and preferably from about 0.1% to about 15%, by weight based on the dry weight of the total carrier composition.

Enhancers for use in the drug carrier composition and polymeric coating may be selected differently in cases where it might be desirable to use differing processing conditions for the drug carrier composition and polymeric coating, for example to prevent drug loss where high or excess drug concentration or loading in the carrier composition. Enhancers for use with the polymeric coating may be selected with sufficiently high boiling points or lower volatile reactivity within the coating to withstand prolonged exposure to elevated processing temperatures employed to drive off the solvents therein, and include monovalent, saturated and unsaturated aliphatic and cycloaliphatic alcohols having 6 to 12 carbon atoms such as cyclohexanol, lauryl alcohol and the like; aliphatic and cydoaliphatic hydrocarbons such as mineral oils; cycloaliphatic and aromatic aldehydes and ketones such as cyclohexanone; N,N-di (lower alkyl) acetamides such as N,N-diethyl acetamide, N,N-dimethyl acetamide, N-(2-hydroxyethyl) acetamide, and the like; aliphatic and cycloaliphatic esters such as isopropyl myristate and lauricidin; N,N-di (lower alkyl) sulfoxides such as decylmethyl sulfoxide; essential oils; nitrated aliphatic and cycloaliphatic hydrocarbons such as N-methyl-2-Pyrrolidone, Azone; salicylates, polyalkylene glycol silicates; aliphatic acids such as oleic acid and lauric acid, terpenes such as cineole, surfactants such as sodium lauryl sulfate, siloxanes such as hexamethyl siloxane; polyethylene glycols, polypropylene glycols, and polyether polyols, epoxidized linseed oils, simple liquid esters, and the like, alone or in combination.

On the other hand, enhancers selected for use with the drug carrier composition may be those with lower boiling points or higher relative volatility or reactivity within the carrier composition since exposure to elevated processing temperatures is decreased, and therefore their loss, similar to drug loss, is decreased. Such enhancers are well known in the art and examples include alcohols, propylene glycol, dipropylene glycol, butylene glycol, m-pyrol, with propylene glycol being preferred.

In addition to enhancers, there may also be incorporated various pharmaceutically acceptable additives and excipients available to those skilled in the art. These additives include tackifying agents such as aliphatic hydrocarbons, mixed aliphatic and aromatic hydrocarbons, aromatic hydrocarbons, substituted aromatic hydrocarbons, hydrogenated esters, polyterpenes, silicone fluid, mineral oil and hydrogenated wood rosins. Additional additives include binders such as lecithin which "bind" the other ingredients, or rheological agents (thickeners) containing silicone such as fumed silica, reagent grade sand, precipitated silica, amorphous silica, colloidal silicon dioxide, fused silica, silica gel, quartz and particulate siliceous materials commercially available as Syloid®, Cabosil®, Aerosil®, and Whitelite®, for purposes of enhancing the uniform consistency or continuous phase of the composition or coating. Other additives and excipients include diluents, stabilizers, fillers, clays, buffering agents, biocides, humectants, anti-irritants, antioxidants, preservatives, plasticizing agents, cross-linking agents, flavoring agents, colorants, pigments and the like. Such substances can be present in any amount sufficient to impart the desired properties to the composition or coating. Such additives or excipients are typically used in amounts up to 25%, and preferably from about 0.1% to about 10%, by weight based on the dry weight of the total carrier or polymeric coating composition.

Transdermal system 10 further employs release liners or removable/peelable covers and backings to protect and/or anchor the system or its components during manufacturing as described herein, or thereafter, and to enable handling and transportation.

The release liner is typically impermeable and occlusive, and must be compatible with the particular polymers or active agents so as not to interfere with the composition's ultimate application and therapeutic effect. Some suitable materials that can be used, singularly, in combination, as laminates, films, or as coextrusions, to form the release liner are well known in the art. When the release liner is composed of a material which typically does not readily release (i.e., is not easily removed or separated from the coating or composition to which it is affixed), for example paper, a releasable material such as a silicone, Teflon®, or the like may be applied to the surface by any conventional means. Preferred release liners are films commercially available from DuPont, Wilmington, Del., under the trademarks Mylar®, and fluoropolymer (silicone) coated films commercially available from Rexam Release, Oak Brook, Ill. under the trademarks FL2000® and MRL2000®, and from 3M Corporation, St. Paul, Minn. Sold under the trademarks ScotchPak® such as 1022.

The backing is typically moisture impermeable and flexible but should be compatible with the particular polymers or active agents used so as not to interfere with the composition's ultimate application and therapeutic effect. Some suitable materials that can be used, singularly, in combination, as laminates, films or as coextrusions, to form the backing layer 20 are also well known in the art and include films or sheets of polyethylene, polyester, polypropylene, polyurethane, polyolefin, polyvinyl alcohol, polyvinyl chloride, polyvinylidene, polyamide, vinyl acetate resins, BAREX®, ethylene/vinyl acetate copolymers, ethylene/ethylacrylate copolymers, metal-vapor deposited films or sheets thereof, rubber sheets or films, expanded synthetic resin sheets or films, non-woven fabrics, fabrics, knitted fabrics, clothes, foils and papers. The backing layer 20 may generally have a thickness in the range of 2 to 1000 micrometers. The backing layer 20 may be pigmented, for example colored to either match with or conversely easily distinguish from the site of application, and/or contain printing, labeling and other means of identification and/or traceability of the transdermal unit or system itself. The backing layer 20 may further be made opaque or substantially opaque (i.e., preventing light or certain energy wavelengths from penetrating or passing through), such as by metallization, fillers, inks, dyes and the like, for purposes of protecting photosensitive active agents from degradation and/or preventing photoallergic reactions or irritations on the subject.

The drug carrier and polymeric coating comprising the present invention can be prepared in any manner known to those of skill in the art. In the manufacture of a transdermal system 10 according to the present invention, drug carrier composition layer 12 and the non-drug loaded polymeric and/or adhesive coating 18 may be prepared and processed separately, and then combined. It should be understood, however, that if drug or solvent loss is not critical to the formulation of the transdermal system, drug carrier composition layer 12 and the non-drug loaded polymeric and/or adhesive coating 18 may be prepared separately and processed together.

One method of preparing transdermal system 10 is as follows:

1. Appropriate amounts of the polymer(s), adhesive(s), solvent(s), co-solvent(s), enhancer(s), additive(s) and/or excipient(s) are combined and thoroughly and uniformly mixed together in a vessel to form the non-drug loaded polymeric coating.

2. The polymeric coating is then transferred to a coating operation where it is cast onto a backing film/layer at a controlled specified thickness and exposed to elevated temperatures, such as in an oven, to remove the volatile processing solvents.

3. The polymeric coating is then laminated to a release liner applied to the surface opposite the backing/layer and wound into rolls.

4. Appropriate amounts of drug(s), polymer(s), adhesive(s), solvent(s), co-solvent(s), enhancer(s), additive(s) and/or excipient(s) are combined and thoroughly and uniformly mixed together in a vessel to form the active agent carrier composition.

5. The composition is then transferred to a coating operation where it is cast onto a release liner at a controlled specified thickness and exposed to elevated temperatures, such as in an oven, to remove the volatile processing solvents.

Figure 2:
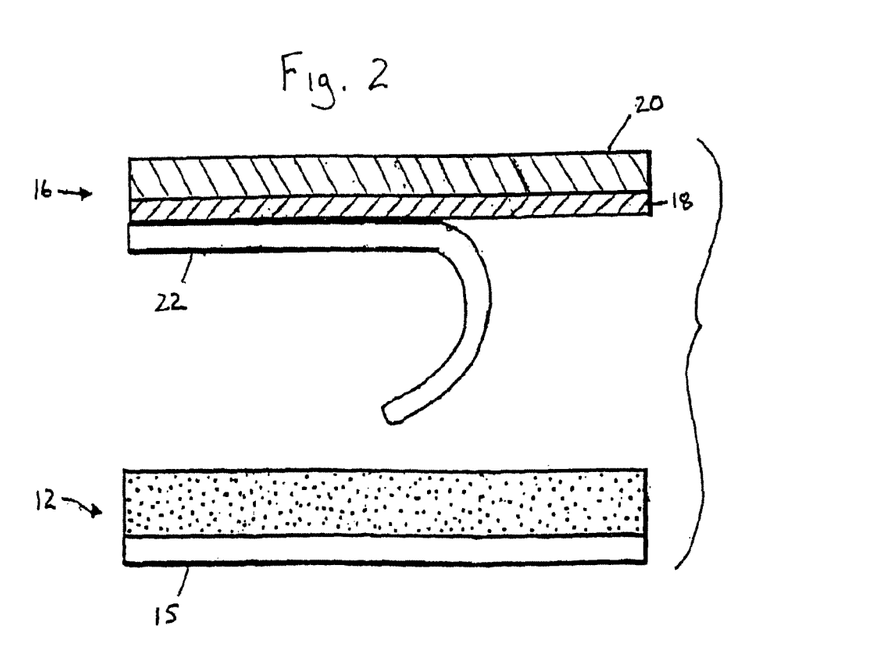
FIG. 2 shows a schematic cross-section of the agent-carrier assembly and backing assembly according to the embodiment of the present invention as shown in FIG. 1, prior to lamination together.

6. As depicted in FIG. 2, the release liner 22 that is affixed to the polymeric coating 18 to form the backing composite 16 is then removed and affixed to the exposed surface of the drug carrier composition 12, and the laminated assembly is wound into rolls.

7. Thereafter, desired size and shape delivery systems 10 are prepared by die-cutting or the like, from the rolled laminate and then packaged.

Alternatively, the release liner 22 may not be necessary if both the agent-carrier composition 12 and backing composite 16 are produced concomitantly, wherein attachment to each other could be performed after processing of each individually, such as in an in-line process, thereby avoiding step 3 above. As described earlier, either the drug carrier composition 12 or the polymeric coating 18 may be an adhesive or pressure-sensitive adhesive, allowing pressure lamination to each other by their adhesive qualities. However, where a release liner 22 is employed in the manufacturing steps, it is preferable to affix it to the polymeric coating and not the drug carrier composition to prevent any further drug loss that could occur from winding into rolls and subsequent removal of such release liner, or the failure of release liner 22 to adhere to the drug carrier composition.

Additionally and alternatively, a separate adhesive may be used to (a) affix the backing composite 16 to the drug carrier composition 12 at the surface opposite the release liner 15 and/or (b) affix the polymeric coating or the drug carrier composition, depending on which is to be used as the point of topical application to the skin or mucosa, to either the backing film/layer or the release liner.

In certain other preferred embodiments, a non-woven drug permeable film/layer, such as a polyester film, may be interdisposed, such as pressure lamination, for structural support or ease of manufacturing (i.e., has no effect on controlling drug permeation or delivery) between the non-drug loaded coating and the drug-loaded carrier composition.

In cases where it might be desirable to use differing processing conditions for the drug carrier composition and the polymeric coating, for example to prevent drug loss where there is high or excess drug concentration or loading in the carrier composition, or where the drug degrades by exposure to atmospheric air, or that employ use of volatile enhancers, particular care may need to be employed to avoid prolonged processing times or exposure to air during manufacturing. In this regard, controlled manufacturing environments, for example employing lower temperatures or pressures, employing faster processing speeds during exposure to the elevated temperature used to remove solvents, modifying atmospheric gases present (such reduced carbon dioxide levels or using nitrogen in place of air), or modifying air or gas flow (such as during oven drying to remove solvents) at various stages during the process, may also be necessary or desirable.

The order of the processing steps, the amount of the ingredients, and the amount and time of agitation or mixing may be important process variables which will depend on the specific polymers, active agents, solvents or co-solvents, enhancers and additives and excipients used in the transdermal system. These factors can be adjusted by those skilled in the art, while keeping in mind the objects of achieving the interaction between the drug carrier composition and the non-drug loaded coating. It is believed that a number of other methods, for example, other methods of coating that are well-known in the art, such as Mayer rod, gravure, knife-over roll, extrusion, casting, calendaring and molding, or changing the order of certain steps, can be carried out and will also give desirable results.

Further details and examples of pressure-sensitive adhesives, enhancers, solvents, co-solvents, release liners, backing layers, and other additives, as well as transdermal systems generally, suitable in practicing the invention are described in U.S. Pat. Nos. 5,474,787, 5,958,446, 6,024,976, 6,562,363 and 60/488,928, all of which are assigned to Noven Pharmaceuticals, Inc. and incorporated herein by reference.

EXAMPLES

Figure 3:
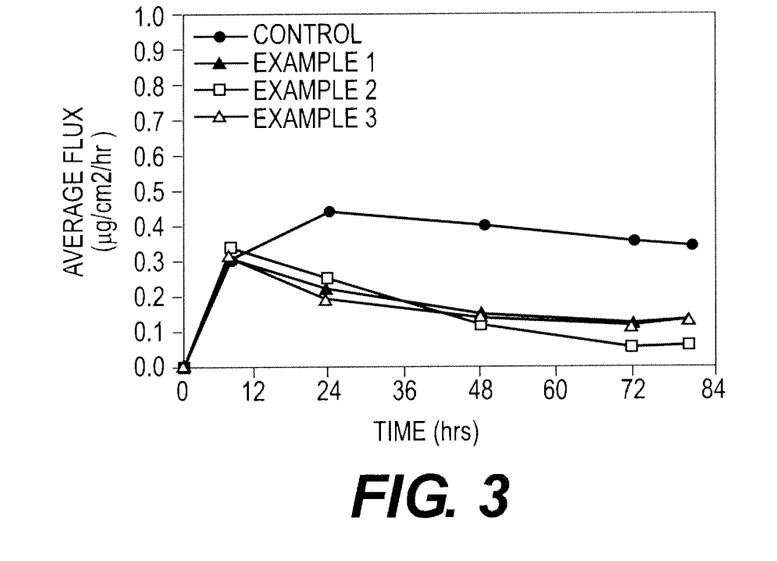
FIG. 3 is a graphic representation of the effects on drug delivery, onset and profile of estradiol with different functionalities/moieties of acrylic-based adhesives in the polymeric coating.
Figure 4:
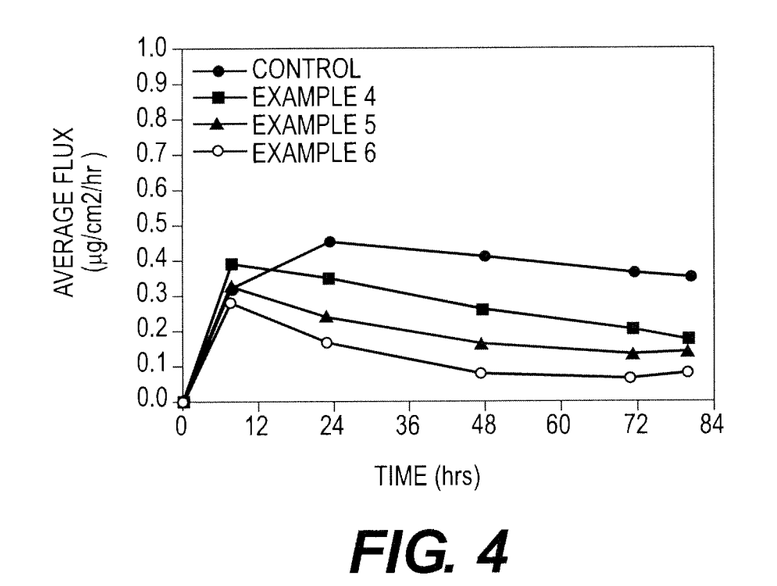
FIG. 4 is a graphic representation of the effects on drug delivery, onset and profile of estradiol with varying coat weights of an acrylic-based adhesive coating.

In the Examples as shown with respect to FIGS. 3-4, the effect of variations in the non-drug loaded coating are determined, indicating the effective control of permeation rate, onset and profile thereby. Referring to the most preferred embodiment depicted in FIG. 1, while the Examples are directed to formulations using estradiol and an acrylic-based adhesive coating, it should be understood that similar drug modulation can be achieved with other active agents, and through the use of other polymers and system configurations as discussed.

All drug-loaded carrier compositions containing estradiol were prepared and coated onto a fluoropolymer release liner and dried for 5 minutes at RT and 5 minutes in a 92° C. oven to produce a pressure-sensitive adhesive carrier composition by dry weight of 20% acrylate pressure-sensitive adhesive (GMS 788), 56% silicone pressure-sensitive adhesive (BIO-PSA-4502), 8% soluble povidone, 6% oleyl alcohol, 8% dipropylene glycol and 2% estradiol at coat weight of about 5 mg/cm$^2$. All studies were conducted relative to a control transdermal delivery system, that being an estrogen transdermal delivery system (Vivelle Dot® manufactured by the assignee of the instant invention, Noven Pharmaceuticals, Inc.), having a known permeation rate, onset and profile.

The non-drug loaded acrylic-based adhesive coatings were varied to determine the effect of the non-drug loaded layer 18 on controlling permeation rate and drug delivery profile of estradiol. As can be seen from the Examples and FIGS. 3-4, control of estradiol delivery profile can be achieved by the use of different moieties in the acrylic polymer backing, the coat weight of the acrylic backing film had a more substantial effect on the permeation rate of estradiol rather than the delivery profile, and varying the thickness and/or moiety of the acrylic polymer backing can modify the drug delivery profile and permeation rate of estradiol.

Determination of drug flux of the described formulations was conducted on a modified Franz Diffusion cell through a disc of stratum corneum obtained from human cadaver skin. The transdermal systems were die-cut and mounted on the disc, and placed on the cell, which contained an isotonic saline solution. The cells were stored at 32° C. for the duration of each flux study while having the solution stirred at a constant rate of approximately 300 rpm. Samples (n=5) of the solution were taken at various time points over the study duration (9 hours), and drug concentrations were determined by high pressure liquid chromatography.

Examples 1-3

In Examples 1-3, the three acrylic coated backings utilized different moieties of acrylic polymer in their composition: Example 1 contains an acid functional moiety, Example 2 contains a non-functional/non-reactive moiety, and Example 3 contains a hydroxyl (—OH) functional moiety. The acrylic coating on the backing had a coat weight of 5.0 mg/cm$^2$ and was coated onto a polyester film. The drug-in-adhesive matrix had a coat weight of 5.0 mg/cm$^2$.

FIG. 3 illustrates the results for the three moieties of the acrylic-based polymer backings utilized. Acid functional and hydroxyl functional acrylic polymer backings had a similar effect on the delivery profile of estradiol. The non-functional/non-reactive moiety in the acrylic backing exhibited a decrease in the delivery profile after 48 hours of delivery compared to the acid functional and hydroxyl functional acrylic backings.

Example 4-6

In Examples 4-6, a single acid functional acrylic polymer backing varying the coat weight was utilized. Coat weights for the acrylic backing were 2.5 mg/cm$^2$, 5.0 mg/cm$^2$, and 10.0 mg/cm$^2$ for Examples 4, 5, and 6, respectively. The results, set forth in FIG. 4, illustrate that the permeation rate decreases as the acid functional acrylic backing thickness increases although the drug delivery profile appears to remain the same, at or near zero-order, for all three coat weights. The drug-in-adhesive matrix had a coat weight of 5.0 mg/cm$^2$.

The examples show that by tailoring the acrylic backing polymer through changes in moiety and thickness one can attain a desired permeation rate and delivery profile for estradiol. As the functional moiety and thickness change, the permeation rate and delivery profile can be changed to create a transdermal patch with a multitude of delivery profiles and rates for a selected therapeutic target.

The above description and examples are only illustrative of preferred embodiments which achieve the objects, features, and advantages of the present invention, and it is not intended that the present invention be limited thereto.

What is claimed is:

1. A transdermal drug delivery system for controlling the flux of a drug, made by a process comprising preparing a composition comprising:
   (i) a backing layer;
   (ii) an adhesive coating layer comprising an acrylic-based polymer, wherein said adhesive coating layer does not include any drug at the time of preparation, and wherein a first surface of said adhesive coating layer is affixed to one surface of said backing layer;
   (iii) a carrier composition layer comprising an acrylic-based polymer, wherein said carrier composition layer includes an excess drug concentration, wherein said excess drug is present in a solid crystalline form at the time of preparation, and wherein a first surface of said carrier composition layer is affixed to a second surface of said adhesive coating layer; and
   (iv) a release liner affixed to a second surface of said carrier composition layer; wherein said adhesive coating layer is selected to control the flux of said drug from the transdermal drug delivery composition.

2. The transdermal drug delivery system according to claim 1, wherein said drug comprises estradiol.

3. The transdermal drug delivery according to claim 1, wherein said adhesive coating layer is applied at a coat weight selected to control the flux of said drug from the transdermal drug delivery composition.

4. The transdermal drug delivery according to claim 1, wherein said acrylic polymer of said adhesive coating layer has a monomer content that is selected to control the flux of said drug from the transdermal drug delivery composition.

5. The transdermal drug delivery according of claim 1, wherein said adhesive coating layer has a functionality that is selected to control the flux of said drug from the transdermal drug delivery composition.

6. The transdermal drug delivery system according to claim 1, wherein at least one of said adhesive coating layer and said carrier composition layer comprises a blend of at least one acrylic-based polymer and at least one second polymer selected from the group consisting of silicone-based polymers, rubbers, gums, polyisobutylenes, polyvinylethers, polyurethanes, styrene block copolymers, styrene/butadiene polymers, polyether block amide copolymers, ethylene/vinyl acetate copolymers, vinyl acetate based adhesives, polyvinylpyrrolidones and bioadhesives.

7. The transdermal drug delivery system according to claim 1, wherein at least one of said adhesive coating layer and said carrier composition layer comprises said acrylic-based polymer in an amount from about 2% to about 95% of the total dry weight of the layer.

8. The transdermal drug delivery system according to claim 6, wherein said at least one second polymer includes a silicone-based polymer.

9. The transdermal drug delivery system according to claim 1, wherein at least one of said adhesive coating layer and said carrier composition layer comprises (i) a first acrylic-based polymer having a first functionality and a first solubility parameter for said drug; and (ii) a second acrylic-based polymer having a second functionality and solubility parameter for said drug, wherein the first and second functionalities differ in the amount and type of functional groups, to provide an acrylic-based polymer combination having a net functionality proportional to the ratio of the first and second acrylic based polymers used, and wherein said first and second acrylic-based polymers are present in proportions to provide a net solubility parameter for said drug.

10. The transdermal drug delivery system according to claim 9, wherein the first acrylic based polymer has substantially no functional groups and the second acrylic-based polymer has functional groups.

11. The method according to claim 10, wherein the second acrylic-based polymer has carboxyl and/or hydroxy functional groups.

12. The transdermal drug delivery system according to claim 10, wherein the functional groups are provided by monomer units containing functional groups which are incorporated into the second acrylic-based polymer in an amount of from 0.1 to 20% by weight, based on the dry weight of the second acrylic-based polymer.

13. The transdermal drug delivery system according to claim 10, wherein the functional groups are provided by monomer units containing functional groups which are incorporated into the second acrylic-based polymer in an amount of from 0.1 to 8% by weight, based on the dry weight of the second acrylic-based polymer.

14. The transdermal drug delivery system according to claim 9, wherein the first acrylic-based polymer contains hydroxy functional groups and the second acrylic-based polymer contains carboxy functional groups.

15. The transdermal drug delivery system according to claim 9, wherein the amount of the second acrylic-based polymer is in the range of 20-75 weight % and the amount of the first acrylic-based polymer is in the range of 75 to 20% by weight, all based on the total dry weight of the first and second acrylic-based polymers in said layer.

16. The transdermal drug delivery system according to claim 9, wherein the polymer components of at least one of said adhesive coating layer and said carrier composition layer consist essentially of only the first and second acrylic-based polymers.

17. The transdermal drug delivery system according to claim 1, wherein said acrylic-based polymer of the adhesive coating layer comprises an acrylate or alkyl acrylate monomer selected from the group consisting of acrylic acid, methacrylic acid, methyl acrylate, methyl methacrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate.

18. The transdermal drug delivery system according to claim 1, wherein said acrylic-based polymer of the adhesive coating layer comprises a functional monomer selected from the group consisting of acrylic acid, methacrylic acid, maleic acid, maleic anhydride, hydroxyethyl acrylate, hydroxypropyl acrylate, acrylamide, dimethylacrylamide, acrylonitrile, dimethylaminoethyl acrylate, dimethylaminoethyl methacrylate, tertbutylaminoethyl acrylate, tert-butylaminoethyl methacrylate, methoxyethyl acrylate and methoxyethyl methacrylate.

19. The transdermal drug delivery system according to claim 1, wherein said adhesive coating layer is applied at a coat weight of from about 2.5 to about 15 mg/cm$^2$.

20. A transdermal drug delivery system comprising:
(i) a backing layer;
(ii) an adhesive coating layer comprising an acrylic-based polymer, wherein said adhesive coating layer does not include any drug at the time of preparation, and wherein a first surface of said adhesive coating layer is affixed to one surface of said backing layer;
(iii) a carrier composition layer comprising an acrylic-based polymer, wherein said carrier composition layer includes an excess drug concentration, wherein said excess drug is present in a solid crystalline form at the time of preparation, and wherein a first surface of said carrier composition layer is affixed to a second surface of said adhesive coating layer; and
(iv) a release liner affixed to a second surface of said carrier composition layer; wherein said adhesive coating layer is selected to control the flux of said drug from the transdermal drug delivery composition.

* * * * *